(12) United States Patent
Terwee et al.

(10) Patent No.: US 7,182,780 B2
(45) Date of Patent: Feb. 27, 2007

(54) DEVICE FOR USE IN EYE SURGERY

(75) Inventors: Thomas Terwee, Roden (NL); Steven Koopmans, Groningen (NL)

(73) Assignee: AMO Groningen, B.V., Groningen (NL)

( * ) Notice: Subject to any disclaimer, the term of this patent is extended or adjusted under 35 U.S.C. 154(b) by 0 days.

(21) Appl. No.: 09/996,290

(22) Filed: Nov. 28, 2001

(65) Prior Publication Data
US 2002/0107567 A1   Aug. 8, 2002

(30) Foreign Application Priority Data
Nov. 29, 2000 (SE) ................................. 0004393

(51) Int. Cl.
*A61F 2/16* (2006.01)
(52) U.S. Cl. ..................... 623/6.12; 606/107
(58) Field of Classification Search ............. 623/6.12, 623/6.22, 6.39, 6.4, 6, 905, 90, 7, 4.1; 606/107
See application file for complete search history.

(56) References Cited

U.S. PATENT DOCUMENTS

| 4,608,050 | A | 8/1986 | Wright et al. |
| 4,782,820 | A | 11/1988 | Woods |
| 5,843,184 | A | 12/1998 | Cionni |
| 6,358,279 | B1 * | 3/2002 | Tahi et al. ............... 623/4.1 |
| 6,413,276 | B1 * | 7/2002 | Werblin ............... 623/6.32 |

FOREIGN PATENT DOCUMENTS

| EP | 0493090 | 7/1992 |
| JP | 97-308946 | 11/1997 |
| WO | WO 00499276 | 8/2000 |

\* cited by examiner

*Primary Examiner*—Corrine McDermott
*Assistant Examiner*—Christopher D. Prone
(74) *Attorney, Agent, or Firm*—Advanced Medical Optics, Inc.

(57) ABSTRACT

A method of manufacturing an intraocular lens inside a capsular bag after the natural lens has been removed employs a sealing device comprising a plug part adapted to seal a rhexis in a capsular bag, thus preventing displacement through the rhexis of a lens-forming liquid material injected through the rhexis and adapted to replace the natural lens and form an intraocular lens implant. The plug part has a slightly larger area than the capsulorhexis and is made of a deformable polymer. The sealing device further comprises an adjusting means connected to the plug part and adapted to position the plug part to a desired location.

37 Claims, 2 Drawing Sheets

DEVICE FOR USE IN EYE SURGERY

FIELD OF THE INVENTION

The present invention relates to a sealing device comprising a plug part adapted to seal a capsulorhexis of a capsular bag used in surgical processes involving insertion of lens-forming liquid to replace the natural lens and forming an intraocular lens implant. It also relates to a method providing visual correction including manufacturing an intraocular lens inside a capsular bag after that the natural lens has been removed.

BACKGROUND OF THE INVENTION

A technique for removing a catarcteous and/or presbyopic natural lens from the capsular bag of the eye and replacing it by a lens-forming liquid material injected directly into the capsular bag is under development. This is described in for example the patent application with application number SE 0001934-9. The liquid material is a partially polymerized material, which can undergo a curing process in the eye and thereby form a solid lens implant. The lens implant acts as a substitute for the natural lens and aims to substantially restore the features of the natural lens of the young eye. Materials and methods suitable for injection and subsequent formation of an IOL (Intra Ocular Lens) are disclosed in the patent applications PCT/EP99/07781, PCT/EP99/07780, PCT/EP99/01766 and SE 0001934-9. The defect natural lens matrix can be removed by a conventional surgical method involving an ultrasound probe, such as a phacoemulsification method involving aspiration. In order to facilitate the removal of the lens matrix and the refilling with lens forming liquid material, a capsulotomy i.e. a capsulorhexis is prepared in the anterior wall of the capsular bag. The capsulorhexis is prepared from a circular or essentially circular capsultomy in the capsular bag wall, typically with a diameter of from about 0.5 to about 2.5 mm. An injection syringe needle is inserted through an incision in the eye and through the capsulorhexis into the capsular bag so the lens-forming liquid material can be injected into the capsular bag.

It has been identified as a problem in capsular bag filling processes that during the injection and before the final lens is formed liquid material can leak through the capsulorhexis. For this purpose a plug is proposed in the Japanese patent specification JP97-308946. This plug is adapted to be attached to the injection syringe needle and inserted to the eye and positioned in the right position in the rhexis when the syringe needle is inserted. A problem with this plug is that it is clamped and/or glued in the rhexis. Since the plug is relatively large and adapted to stay in the rhexis permanent optical problems could arise. Furthermore, it needs a relatively large opening in the eye to be implanted. The plug comprises also a filling tube, which has to be cut off after filling. The tube could cause a leak. The size of the plug may also influence the free movement of the capsule that is needed for an even deformation of the capsule during accommodation. In the International Patent Application published as WO 00/49976 (University of Miami), a more simple plug construction is suggested that attempts to act as a valve during the surgical process. Also this plug suffers from the drawback that it permanently locates parts of its structure outside the capsular bag after finalizing the surgery. The curved flexible member is permanently protruding from the capsular bag through its hub like attachment point to the flexible discoid flap-valve member. Consequently, the protruding parts may risk to compromise surrounding delicate eye tissues, including the iris, while they also risk generating unwanted optical side effects. It is therefore obvious that it is need for improvements in plug parts or sealing means for a capsulorhexis that has been introduced in a capsular filling process.

DESCRIPTION OF THE INVENTION

It is an object of the invention to provide a sealing device for a capsulorhexis of the capsular bag of the eye that effectively prevents a liquid inserted into the capsular bag to leak out through the capsulorhexis.

It is also an object of the present invention to provide a sealing device for a capsulorhexis that leaves no permanent parts outside the capsular bag after the lens implantation process is finalized.

Another object is to provide a sealing device having means by which its location can be controlled after its insertion throughout the capsule filling process and lens forming process.

Still a further object of the invention is to provide a sealing device for the capsular bag that can contribute to compensate for refractive errors and/or wavefront aberrations of the optical parts of the eye.

These objects are obtained with a sealing device having a plug part made of a deformable polymer that is capable of admitting the entrance of an injection device for injecting a lens-forming liquid material through the capsulorhexis, while having slightly larger area than the capsulorhexis, so as to obtain a sealing effect from being pressed in a tight sealing position with the inner capsular bag from the pressure exerted by the injected liquid material. The sealing device further comprises an anteriorly protruding removable adjusting means connected to the plug part. By the adjustment means, the plug part can be displaced exactly to the desired location by surgeon. It is an important characteristic of the presently invented sealing device that it is free from any features protruding out from the capsular bag subsequent to the surgical process. This is due to that its adjustment means is readily removable through surgical incision of the eye when the surgeon so decides. The highly simplified construction of the sealing device that leaves no permanent parts outside capsular bag protruding out in posterior chamber of the eye resides from the finding that the fluid lens forming material is capable of exerting a sufficient pressure on the deformable sealing device so it together with the capsular bag wall can act sufficiently sealing without the need of additional securing means.

Preferably, said plug part is essentially disc-shaped and suitably said plug part is adapted to be placed at the inside of the capsular bag, covering the whole capsulorhexis. It is suitable that the plug part has a somewhat larger diameter than the capsulorhexis to enable a safe sealing effect. A suitable plug diameter is accordingly in the range of about 0.5 to about 2.5 mm. However, in certain embodiments described below the plug part can have a considerably larger extension. The plug part of the sealing device is adapted to permanently remain in the eye, but can alternatively, be removed after the lens forming process in the capsular bag is completed and the lens forming material is satisfyingly cured. In such case, the adjustment means are not removed, but employed to carefully loose the plug part and transfer it out of the eye.

The plug part is made of a suitable soft, flexible, biocompatible material that is sufficiently thin to follow the accommodation movements of the capsular bag. Normally that means that the plug part will have a thickness in the range of about 5 to 250 micrometers. In order to avoid any problems of material incompatibility, or eventually any optical side effects, it is preferable that the plug part is made of a similar material to the lens forming material. Preferably the plug part is made from a silicon material to comply with an injectable lens forming silicon material. For the condition that the capsulorhexis is placed in the visual field, it is greatly preferable that the plug part is made of a material having essentially the same refractive index as the material inserted in the capsular bag. This is important especially if the plug part is to be left in the capsular bag after that the lens-forming process is completed. Hereby, the sealing device does not affect the visual quality. Suitable silicone materials can be found among the terpolymers mentioned in PCT/EP99/07781 and PCT/EP99/07780, or the high refractive index silicones, for example, disclosed in U.S. Pat. Nos. 5,236,970 and 5,444,106, optionally without UV absorbers and other additives regarded unsuitable for the present technical application. Also various medical grades of conventional polydimethylsiloxanes (PDMS) are suitable within certain embodiments of the invention. The plug part can be prepared with conventional molding processes for silicones, which together with other suitable silicones than the aforementioned are well known to persons skilled in this technology.

The adjusting means typically is one or several thin flexible wire(s) that is non-permanently attached to the plug part. In a suitable embodiment, the thin wire penetrates the plug part from the anterior to the posterior side and then penetrates the plug part from the posterior to the anterior side. The distance between the two penetrating positions and their locations on the plug part are selected so that it can be comfortably manipulated, either with a microforceps, or with other suitable means, also from outside of the eye. It is to be understood that the thin wire can be of such a length that it protrudes out of the eye through the corneoscleral incision. The wire is preferably made of less flexible material than the material of the plug part and the capsular bag and is attached to the plug part in a manner that is easily can be removed when the lens forming material is introduced, or when then lens forming process is finalized. Typically suitable materials for the wire are different brands of nylons that are well known in surgical processes and not discussed in further detail.

In one aspect of the invention, the plug part of the sealing device is provided with a contacting means that establishes an improved contact between the anterior surface of the plug part and the inner (posterior) wall of the capsular bag, so to prevent or hinder any displacements of the plug part from forces exerted on the capsular bag wall during the accommodation process. Further, substantial problems to obtain a correct accommodation process may arise if the capsulorhexis to be sealed has a large extension, such as exceeding several millimeters. In order to ensure correct accommodation processes, the forces exerted on the capsular bag needs to be transmitted correctly without any dead zones incapable of participating in the process. When a very soft lens material is employed which has sufficiently low elasticity modulus as to form accommodating lens, this type of dead zones and/or large plug part displacements during accommodation, may eventually cause that lens material does not correctly participate in the accommodation, or at worst will bulge out anteriorly with uncontrollable consequences. To comply with any such unwanted effects, the plug part preferably is provided with contact means to improve the contact between the plug part and the capsular bag wall.

Suitable contact means can be accomplished by providing plug part with an anterior surface that, at least partially, admits an enhanced friction to the inner wall of the capsular bag. As an example, this can be accomplished with the provision of a peripheral ring-shaped roughened anterior surface adapted to improve contact the inner wall of the capsular bag. Hereby, the contact between the sealing device and the inner wall of the capsular bag is improved. Friction enhancing processes and roughening processes are well known to silicon experts and are not elaborated on herein in any detail. Suitably, the whole area designated to contact the capsular bag inner wall is modified or treated accordingly which means that typically that about 5 to 50% of the total surface is modified or treated.

In another aspect of the invention, the plug part of the sealing device has an anteriorly extending ring in the middle with a diameter fitting into the capsulorhexis from below. The ring is adapted to stabilize the correct position of the sealing device.

According to a special embodiment, the plug part has a cut admitting passage of the lens-forming material. Hereby, the sealing device can be more easily retained in its position during the injection of lens forming material. Suitably, the cut is provided with an overlapping part adapted to seal the cut when the injection is completed, in order to prevent from undesired leakage of injected lens-forming material through the cut.

The inventive sealing device can suitably be positioned in a capsulorhexis of about 1 mm in diameter positioned off the optical axis of the eye, i.e. outside the normal visual field. Alternatively, the capsulorhexis includes the optical axis. In such case, it is of importance that the plug part is perfectly optically clear and that it does not contribute to any optical side effects. Preferably, the plug part is then made of a material that has the same or essentially the same refractive index as the lens forming material.

In another embodiment of the invention, the sealing device is designed to have specific predetermined optical characteristics and to be used in the visual field of eye. The sealing device will then have such an extension that it extends over the whole, or substantially the whole, visual field of the eye and can individually tailored for a patient to correct for optical deficiencies, including refractive errors or aberrations typically arriving from individual irregularities of the corneal surfaces. In a surgical correction process, aiming to make use of the optical characteristics of the sealing device, a larger part of the anterior capsular bag can be surgically excised, such as about 2 to 6 mm of the capsular bag surrounding the optical axis. A sealing device having suitable extension to comply with an accordingly excised capsular bag can the be employed in a capsular bag lens filling process that admits visual correction of optical errors also from other parts of the eye, such as the corneal surfaces. The plug part of the sealing device can then be provided with a refractive power or with optical surfaces that can correct for aberrations, such as astigmatism and/or spherical aberration. Typically such a sealing device having lens power can be made in material having different refractive index than the injectable lens forming material and be provided with at least one surface deviating from perfect sphericity, i.e. being aspheric to reduce or eliminate aberrations.

The present invention also relates to a method of performing visual correction that involves the manufacturing of an intraocular lens inside the capsular bag of the eye. The method comprises the steps of:

inserting a sealing device in a capsulorhexis, said plug part being adapted to cover the capsulorhexis from the inside of the capsular bag;

adjusting the location of said sealing device with an adjusting means operable from the outside of the capsular bag;

delivering a lens-forming material through the capsulorhexis into the capsular bag by using a delivering means and by displacing and/or deforming the plug part to admit passage for the material;

removing the delivering means out from the eye, whereby the plug part retains its sealing position, thereby preventing displacement of the lens-forming liquid material out from the capsular bag.

In one embodiment, the method comprises removing the sealing device through the capsulorhexis when the lens-forming process is completed. Otherwise, only the adjusting means is removed when the plug part has been positioned to seal capsulorhexis by the inserted lens-forming material in the capsular bag. Suitably the method comprises deforming the plug part so as to obtain a shape insertable through the capsulorhexis. Preferably the method comprises controlling the position of said plug part by means of the adjusting means.

In one embodiment the method comprises inserting the lens-forming material to the capsular bag through a cut in the plug part and through the capsulorhexis.

The method can also comprise a step where an agent that counteracts secondary cataract is introduced in the capsular bag before introducing the lens forming material. Such agents typically are typically introduced with an injection syringe that can displace or deform the plug part sufficiently to insert a for injection needle in the capsular bag. The plug part provides a sufficiently sealed environment that the injected agent is prevented from coming in contact with other ocular tissues than the inner wall of the capsular bag during the secondary cataract treatment. Suitable agents are cytotoxic or antiproliferative agents that counteracts growth of epithelial cells that can compromise the transparency of the postsurgical capsular bag. An example of such an agent is 5-fluorouracil, but numerous other agents are conceivable to the skilled person. Alternatively an agent capable of blocking epithelial cell adhesiveness would be a useful such as the calcium channel blocker mibefradil.

In a special embodiment the method further comprises measuring the error of refraction of the eye and designing the plug to further compensate for error of refraction. In this embodiment, the method also can comprise measuring one or several aberrations of the cornea by a corneal topographic method or with conducting a wavefront analysis of the aphakic eye during the surgical process, for example with a Hartmann-Scahck sensor equipment, or the similar. The method can also involve estimations of the aberrations that will be generated in a wave front arriving from the lens to be formed in the capsular bag. Preferably, the results from these optical measurements can be employed to design the surface of the plug to compensate for the aberration of the eye, or alternatively to select a sealing device having plug part that will provide the best optical outcome for an individual, among a plurality of sealing devices in a kit with different refractive values and/or aberrations.

It is obvious that the present invention provides a highly advantageous sealing device for use in ophthalmic surgery that admits a high degree of versatility and readily can be adapted for numerous different surgical conditions due to its simplified construction and its adaptability to its ocular environment. The following part aims to exemplify some specific embodiments of sealing devices that aims to be illustrative, but not limiting for the scope of invention.

DETAILED DESCRIPTION OF THE EMBODIMENTS

Figure 1A:
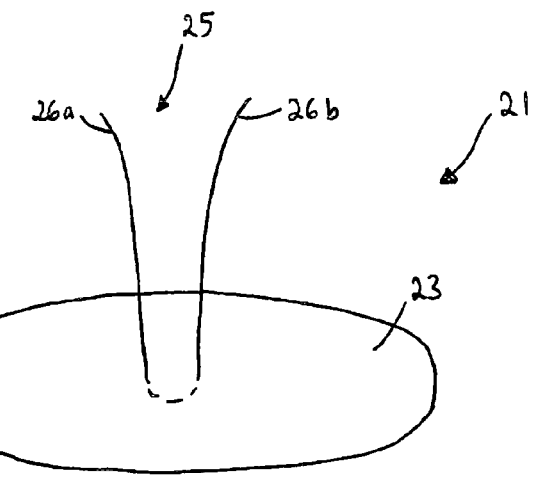
FIG. 1a is a schematic view from above of a sealing device according to a first embodiment of the invention.

FIG. 1a is a schematic view from above of a sealing device 21 according to a first embodiment of the invention. The sealing device 21 comprises an essentially disc-shaped plug part 23 and an adjusting means 25. The plug part 23 is made of a deformable polymer such as a silicon material. In this embodiment the adjusting means 25 is a nylon thread attached at its middle to the center of the plug part 23. For example, the thread can pass through two holes in the plug part 23 leaving the adjusting means 25 with two thread ends 26a and 26b pointing out from the plug part 23 on the same side. This thread 25 could of course be attached to the plug part 23 in some other way and it can be made from another material than nylon. It is also possible to only attach one end of the thread to the plug part 23 leaving only one end pointing out from the plug part 23. The nylon thread used in this embodiment has a suitable stiffness so it enables manipulation of the plug part. The material of the can have a refractive index compatible with the lens material and it should follow the deformation of the capsular bag if the sealing means is adapted to be left in the rhexis.

Figure 1B:
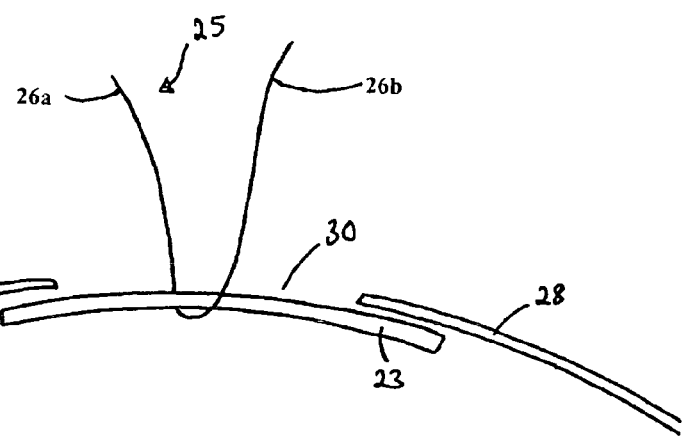
FIG. 1b is a side view of the sealing device in FIG. 1a inserted into a capsular bag.

FIG. 1b is a side view of the sealing device 21 shown in FIG. 1a inserted into a capsular bag 28. The plug part 23 of the sealing device 21 is inserted inside the capsular bag and it is adapted to cover a rhexis 30 in the capsular bag from below. The nylon threads 26a, 26b are extending anteriorly from the sealing device 21 and preferably they are long enough to protrude out of the eye. Thus, the sealing device 21 can be controlled and kept in the desired location from outside the eye. The sealing device 21 is adapted to be inserted into the eye before the lens-forming liquid material is injected and after that the natural lens has been removed.

When the lens-forming material is injected, a delivering means, here an injection syringe is used. The injection syringe needle is inserted through the eye and through the capsulorhexis by sufficiently displacing and/or deforming the sealing device so the needle is admitted into the capsular bag. After the injection the syringe needle is removed out from the capsular bag and the eye and the pressure exerted by the fluid lens-forming material provides the sealing device to retain its original position and shape in front of the rhexis thus preventing the lens-forming material to leak out. The lens-forming material can now be cured into the final lens implant and the wire can be removed from the eye with for example a forceps. To be noted is that the injection syringe not actually needs to be inserted all the way into the capsular bag. It is enough to inject the lens-forming material outside the rhexis in a direction towards the rhexis. Then the material will force itself through the sealing device and into the capsular bag. If a small amount of the material would be left in the anterior chamber of the eye it will easily be flushed out by the rinsing liquid as used during the surgical procedure.

The liquid material can be a silicon material that will cure in ambient body temperature or that will cure through another curing mechanism by means of photosensitizers activated by light of a selected wavelength as further described in PCT/EP99/07781. When the lens-forming fluid has filled the capsular bag the sealing device 21 is pressed against the inner wall around the rhexis of the capsular bag by the lens implant. If the sealing device 21 is adapted to be left in the capsular bag only the adjusting means 25 is removed. Otherwise, the whole sealing means 21 is removed. The plug part 23 could be deformed by an instrument operated from outside the eye such that it can be removed through the rhexis. The position and the size of the rhexis could be the same as described for the first embodiment but if the plug part is adapted to be left in the rhexis the rhexis preferably is positioned so as to include the optical axis. The rhexis is also preferably larger than one mm in diameter and thus the plug part also has to be larger than in the first embodiment to cover the whole rhexis. In fact the plug part preferably covers the whole path of light that is admitted by the pupil. In the case where the plug part 23 is left in the eye the plug part 23 material should also have essentially the same refractive index as the lens-forming material. When the sealing device 1 is left in the rhexis 9 the plug part 2 preferably is made of such a material and has such dimensions that it follows the deformation of the capsular bag as described above. The plug part 23 in this embodiment preferably can be designed to further correct for refractive error in the eye. It can also be designed to correct for aberration defects of the optical surfaces of the eye, such as spherical aberration. The necessary measurements of the aberrations of the eye and the designing of a surface needed to be provided to the plug part 23 to compensate for the aberration are disclosed in detail in the patent application SE 0001925-7 which is incorporated in this application by reference. It is also possible to excise a larger part of the capsular bag wall than demonstrated in FIG. 1b and thereby provide a larger opening of the capsular bag and use a larger sealing device that can extend over the whole visual field. A considerable possibility to provide visual correction that is complementary to what is possible from the injected lens is thereby provided.

Figure 2:
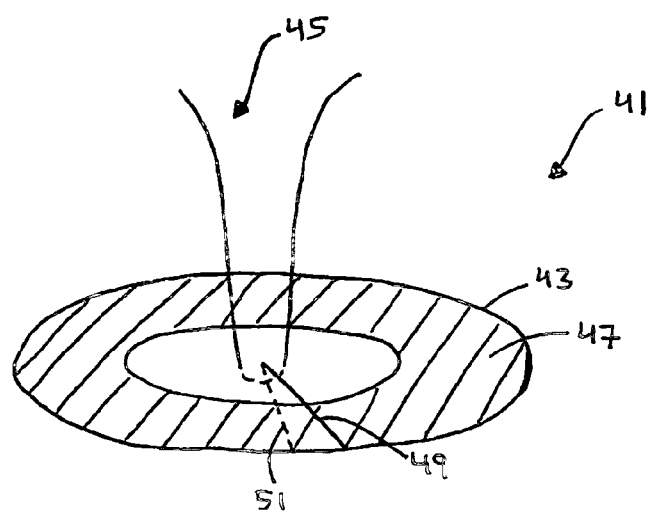
FIG. 2 is a view from above of a second embodiment of the sealing device according to the invention.

FIG. 2 is a view from above of a sealing device 41 according to a second embodiment of the invention. This second embodiment of the sealing device 41 principally follows the first embodiment of the sealing device. It comprises a plug part 43 and an adjusting means 45. The materials and the dimensions are the same and the use of the sealing device is also the same. The difference is that the plug part 43 is provided with a roughened surface 47 on the part of the surface contacting the inner wall of the capsular bag. The purpose of this roughened surface 47 is to keep the sealing device 41 in the desired location covering the rhexis. The plug part 43 comprises also a cut 49 along a radius of the disc-shaped plug part 43. The purpose of the cut 49 is to make it easier for the injection syringe needle to come through the rhexis during the injection and to minimize the leakage of the injected material through the rhexis during the injection. Preferably the plug part 43 also is provided with an overlapping part 51 under the cut 49. The purpose of the overlapping part 51 is to prevent the material from leaking out through the cut 49 after the needle has been removed. As explained above it is not necessary to insert the injection syringe needle all the way through the rhexis to insert the lens-forming material. However, the cut 49 also in this case simplifies the injection.

Figure 3:
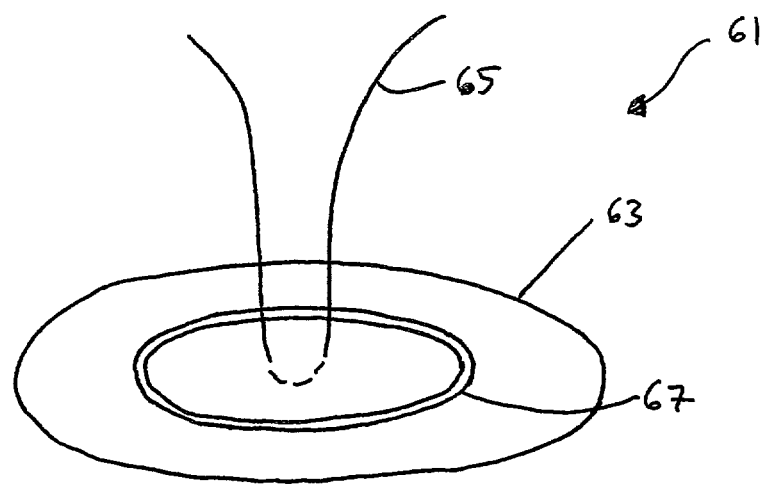
FIG. 3 is a view from above of a third embodiment of the sealing device according to the invention.

FIG. 3 is a view from above of a sealing device 61 according to a third embodiment of the invention. Also this third embodiment of the sealing device 61 principally follows the first embodiment of the sealing device. It comprises a plug part 63 and an adjusting means 65. The materials and the dimensions are the same and the use of the sealing device is also the same. The difference is that the plug part 63 comprises on the surface from which the adjusting means 65 protrudes an anteriorly protruding ring 67 with a slightly smaller diameter than the diameter of the rhexis. This ring 67 is adapted to fit into the rhexis when the plug part 63 has been located in the capsular bag so as to keep the sealing device 61 in the correct position sealing the rhexis from the inside of the capsular bag.

Figure 4:
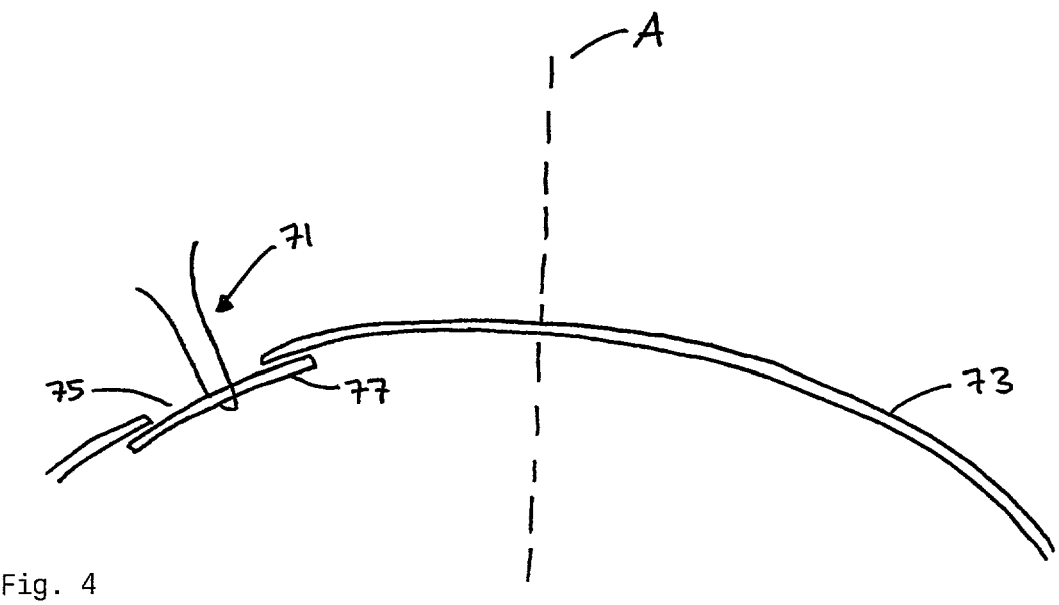
FIG. 4 is a side view of a sealing device according to the invention inserted into a capsular bag.

FIG. 4 is a side view of a sealing device 71 of any of the above mentioned kind inserted into a capsular bag 73 through a rhexis 75. The rhexis 75 is in this case located off the optical axis A of the eye. The rhexis 75 has here a diameter of only about 1 mm and a plug part 77 of the sealing device 71 has thus a slightly larger diameter. The sealing device 71 could in this case either be left in the capsular bag 73 since it is located off the optical axis and not will disturb the vision or be removed from the eye. The removing of the sealing device 71 is easier in this case when the sealing device is smaller.

Of course the different described features in all these embodiments can be combined in all possible ways.

The invention claimed is:

1. A method of performing visual correction in a patient by replacing the natural lens with a lens implant, comprising:
   (a) excising an area of the anterior capsular bag of the eye having a sufficient size to surgically remove the natural lens;
   (b) locating a sealing device comprising a flexible plug part and removable adjusting means of a size sufficient to cover said excised area with said adjusting means to a position where a peripheral anterior surface of said plug part contacts the inner wall of the capsular bag so as to sufficiently cover said excised area, without additional sealing means, wherein the adjusting means protrudes outside the eye and is operated from outside of the eye to locate the sealing device;
   (c) delivering a lens filling material into the capsular bag by using a delivering means to temporarily displace and/or deform said plug part to admit passage into the capsular bag of said material;
   (d) before removing the delivery means, introducing lens forming material into the capsular bag to an extent that said material exerts a sufficient pressure on the posterior side of the plug part to seal the excised area without additional sealing means, so said lens material is prevented from being displaced from the capsular bag to the posterior chamber of the eye; and
   (e) finalizing the lens forming process in the eye,
   wherein the adjusting means of the sealing device is removed from the eye after completing the introduction of lens forming material into the capsular bag.

2. A method according to claim 1, wherein said excised area is intersected by the optical axis.

3. A method according to claim 2, wherein said excised area is of a size sufficient to essentially extend over the visual field.

4. A method according to claim 1, comprising removing the adjusting means of the sealing device from the eye upon finalizing the lens forming process.

5. A method according to claim 1, comprising introducing an agent capable of counteracting the formation of a secondary cataract by epithelial cell growth on the capsular bag inner wall, before delivering the lens forming material.

6. A method according to claim 1, comprising the step of introducing the lens-forming material to the capsular bag through a cut in the plug part.

7. A method according to claim 1, comprising measuring the corneal topography of the cornea and thereby the amount of aberrations of a wavefront arriving from the cornea and selecting a sealing device having a plug part with at least one surface that is capable of compensating for at least one such aberration.

8. A method according to claim 7, including estimating at least one aberration of the lens to be formed in the capsular bag and selecting a sealing device having a plug part which together with said implanted lens is adapted to compensate for at least one such aberration.

9. A method according to claim 7, comprising introducing an agent capable of counteracting the formation of a secondary cataract by epithelial cell growth on the capsular bag inner wall, before delivering the lens forming material.

10. A method according to claim 1, wherein the sealing device is located to a position where the sealing device does not contact an outer wall of the capsular bag.

11. A sealing device according to claim 1, wherein the plug part is adapted to seal a capsulorhexis of a capsular bag without the sealing device contacting an outer wall of the capsular bag.

12. A sealing device for use in ophthalmic surgery to replace a cataractous and/or presbyopic natural lens, comprising a flexible plug part adapted to seal a capsulorhexis of a capsular bag without additional sealing means and to admit an injection device for injecting a lens-forming liquid material through the capsulorhexis without additional sealing means, said plug part having slightly larger area than the capsulorhexis and being made of a deformable polymer, wherein said sealing device further comprises an anteriorly protruding removable adjusting means comprising at least one flexible thread connected to and protruding in an anterior direction from the plug part, wherein said at least one thread is of a length sufficient to protrude outside the eye and can be manipulated from outside the eye to position said plug part to a desired location.

13. A sealing device according to claim 12, wherein the sealing device is free from any parts protruding out from the capsular bag subsequent to the surgical process.

14. A sealing device according to claim 12, wherein said plug part is essentially disc-shaped.

15. A sealing device according to claim 12, wherein said plug part is made of a suitable soft material and is sufficiently thin to follow accommodation movements of the capsular bag.

16. A sealing device according to claim 12, wherein said plug part is made of a silicon material.

17. A sealing device according to claim 12, wherein said plug part is made of a material having essentially the same refractive index as the material inserted in the capsular bag.

18. A sealing device according to claim 12, wherein the plug part is provided with contacting means to the capsular bag, wherein the contacting means is adapted to ensure that a correct accommodating process is established.

19. A sealing device according to claim 18, wherein said contact means comprises a friction-enhanced part of an anterior surface of the posterior plug.

20. A sealing device according to claim 19, wherein at least a surface contacting the inner wall of the capsular bag has a roughened surface.

21. A sealing device according to claim 12, including an anteriorly extending ring in the middle with a diameter adapted to fit into the rhexis from below, the ring being adapted to stabilize the position of the sealing device in the rhexis.

22. A sealing device according to claim 12, wherein the plug part is provided with a cut adapted to admit passage of a lens-forming material.

23. A sealing device according to claim 22, wherein the cut is provided with an overlapping part adapted to seal the cut when the injection is completed.

24. A sealing device according to claim 12 adapted to be positioned in a rhexis of about 1 mm in diameter positioned off the optical axis of the eye.

25. A sealing device according to claim 12 adapted to be positioned in a rhexis of more than 1 mm in diameter positioned to include the optical axis of the eye.

26. A sealing device according to claim 25, wherein said plug part is optically clear.

27. A sealing device according to claim 25, wherein said plug part is adapted to cover the whole path of light that is admitted by the pupil.

28. A sealing device according to claim 27, adapted to compensate for aberration.

29. A sealing device according to claim 23, adapted to correct for error of refraction in the eye.

30. A sealing device according to claim 12, wherein the plug part is adapted to remain in the capsular bag after an intraocular lens-forming process is completed.

31. A sealing device according to claim 12, adapted to be removed after the intraocular lens-forming process is completed.

32. A method of obtaining visual correction subsequent to surgically removing the natural lens, comprising the steps of:
   inserting a plug part of a sealing device comprising a plug part without additional sealing means through a capsulorhexis, said plug part being adapted to cover and seal the capsulorhexis from the inside of the capsular bag without additional sealing means;
   adjusting the location of said plug part with an adjusting means operable from the outside of the capsular bag, wherein the adjusting means protrudes outside the eye and is operated from outside the eye to locate the sealing device;
   delivering a lens-forming material through the capsulorhexis into the capsular bag by using a delivering means and by displacing and/or deforming the plug part to admit the material;
   removing the delivering means from the eye; and
   removing the adjusting means when the plug part seals the capsulorhexis by the influence of the lens-forming material in the capsular bag,
   whereby the plug part retains a sealing position without additional sealing means, thereby preventing displacement of the lens-forming liquid material from the capsular bag.

33. A method according to claim 32, comprising introducing an agent capable of counteracting the formation of a secondary cataract by epithelial cell growth on the capsular bag inner wall, before delivering the lens forming material.

34. A method according to claim 32, further comprising measuring the error of refraction of the eye and optionally selecting a sealing device having a plug part capable of at least partially compensating for an error of refraction.

35. A method according to claim 32, further comprising measuring the corneal topography of the cornea and thereby the amount of aberrations of a wavefront arriving from the cornea, and selecting a sealing device having a plug part with at least one surface that is capable of compensating for at least one such aberration.

36. A method according to claim 32, including estimating at least one aberration of the lens to be formed in the capsular bag and selecting a sealing device having a plug part which is adapted, together with an implanted lens, to compensate for at least on such aberration.

37. A method according to claim 32, wherein the sealing device is located to a position where the sealing device does not contact an outer wall of the capsular bag.

* * * * *